(12) United States Patent
Zvuloni et al.

(10) Patent No.: US 8,066,697 B2
(45) Date of Patent: *Nov. 29, 2011

(54) MULTIPLE CRYOPROBE DELIVERY APPARATUS

(75) Inventors: Roni Zvuloni, Haifa (IL); Shaike Schatzberger, Haifa (IL)

(73) Assignee: Galil Medical Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/640,309

(22) Filed: Dec. 18, 2006

(65) Prior Publication Data

US 2007/0167938 A1    Jul. 19, 2007

Related U.S. Application Data

(63) Continuation of application No. 10/660,478, filed on Sep. 12, 2003, now Pat. No. 7,150,743, which is a continuation of application No. 09/860,486, filed on May 21, 2001, now Pat. No. 6,706,037.

(60) Provisional application No. 60/242,455, filed on Oct. 24, 2000.

(51) Int. Cl.
*A61B 18/02* (2006.01)

(52) U.S. Cl. .......... 606/21; 606/20; 606/22; 606/23

(58) Field of Classification Search ........... 606/20–23
See application file for complete search history.

(56) References Cited

U.S. PATENT DOCUMENTS

| 636,013 | A | | 10/1899 | Tolle | |
|---|---|---|---|---|---|
| 862,867 | A | | 8/1907 | Eggleston | |
| 2,700,876 | A | | 2/1955 | Gagnan | |
| 3,266,492 | A | * | 8/1966 | Steinberg | 606/23 |
| 3,524,714 | A | | 8/1970 | Grove et al. | |
| 3,664,344 | A | * | 5/1972 | Bryne | 606/23 |
| 3,864,060 | A | | 2/1975 | Hall et al. | |
| 3,963,377 | A | | 6/1976 | Elliott et al. | |
| 4,015,606 | A | * | 4/1977 | Mitchiner et al. | 606/23 |
| 4,207,897 | A | * | 6/1980 | Lloyd et al. | 606/23 |
| 4,515,516 | A | | 5/1985 | Perrine et al. | |
| 4,673,415 | A | | 6/1987 | Stanford | |
| 4,750,869 | A | | 6/1988 | Shipman, III | |
| 5,108,390 | A | * | 4/1992 | Potocky et al. | 606/21 |
| 5,133,360 | A | | 7/1992 | Spears | |
| 5,224,930 | A | | 7/1993 | Spaeth et al. | |

(Continued)

FOREIGN PATENT DOCUMENTS

DE    2332513    1/1975

(Continued)

OTHER PUBLICATIONS

Communication Pursuant to Article 96(2) EPC Dated Dec. 5, 2003 From the European Patent Office Re.: Application No. 00650043.3.

(Continued)

*Primary Examiner* — Roy Gibson
*Assistant Examiner* — Kaitlyn Smith
(74) *Attorney, Agent, or Firm* — Fredrikson & Byron, P.A.

(57) ABSTRACT

A cryosurgery apparatus is disclosed. The cryosurgery apparatus an introducer having a hollow and a distal portion, the distal portion being sufficiently sharp so as to penetrate into a body, the hollow of the introducer being designed and constructed for containing a plurality of cryoprobes each of the cryoprobes being for effecting cryoablation, such that each of the plurality of cryoprobes is deployable through the distal portion of the introducer when the distal portion is positioned with respect to a tissue to be cryoablated.

15 Claims, 4 Drawing Sheets

U.S. PATENT DOCUMENTS

| | | | |
|---|---|---|---|
| 5,259,366 A | 11/1993 | Reydel et al. | |
| 5,279,570 A * | 1/1994 | Dombrowski et al. | 604/164.01 |
| 5,281,215 A * | 1/1994 | Milder | 606/20 |
| 5,342,295 A * | 8/1994 | Imran | 604/43 |
| 5,421,323 A | 6/1995 | Herrmann et al. | |
| 5,452,582 A * | 9/1995 | Longsworth | 62/51.2 |
| 5,540,062 A | 7/1996 | Maytal | |
| 5,647,868 A | 7/1997 | Chinn | |
| 5,716,353 A | 2/1998 | Matsuura et al. | |
| 5,735,847 A * | 4/1998 | Gough et al. | 606/41 |
| 5,746,736 A | 5/1998 | Tankovich | |
| 5,759,182 A | 6/1998 | Varney et al. | |
| 5,800,379 A * | 9/1998 | Edwards | 604/22 |
| 5,800,484 A | 9/1998 | Gough et al. | |
| 5,800,487 A * | 9/1998 | Mikus et al. | 607/105 |
| 5,807,083 A | 9/1998 | Tomoiu | |
| 5,846,181 A | 12/1998 | Heckele et al. | |
| 5,853,368 A * | 12/1998 | Solomon et al. | 600/439 |
| 5,899,897 A | 5/1999 | Rabin et al. | |
| 5,902,299 A | 5/1999 | Jayaraman | |
| 5,916,212 A * | 6/1999 | Baust et al. | 606/22 |
| 5,938,658 A * | 8/1999 | Tu | 606/41 |
| 5,964,796 A | 10/1999 | Imran | |
| 5,978,697 A | 11/1999 | Maytal et al. | |
| 5,993,172 A | 11/1999 | Schuman et al. | |
| 5,993,444 A * | 11/1999 | Ammar et al. | 606/21 |
| 5,993,471 A | 11/1999 | Riza et al. | |
| 6,004,273 A | 12/1999 | Sakamoto et al. | |
| 6,009,877 A * | 1/2000 | Edwards | 128/898 |
| 6,016,452 A * | 1/2000 | Kasevich | 607/101 |
| 6,027,497 A | 2/2000 | Daniel et al. | |
| 6,039,730 A | 3/2000 | Rabin et al. | |
| 6,053,937 A * | 4/2000 | Edwards et al. | 607/104 |
| 6,090,105 A * | 7/2000 | Zepeda et al. | 606/41 |
| 6,106,518 A | 8/2000 | Wittenberger et al. | |
| 6,126,654 A | 10/2000 | Giba et al. | |
| 6,129,670 A | 10/2000 | Burdette et al. | |
| 6,132,425 A * | 10/2000 | Gough | 606/41 |
| 6,139,544 A * | 10/2000 | Mikus et al. | 606/21 |
| 6,142,991 A * | 11/2000 | Schatzberger | 606/21 |
| 6,152,894 A | 11/2000 | Kubler | |
| 6,179,831 B1 | 1/2001 | Bliweis | |
| 6,190,378 B1 | 2/2001 | Jarvinen | |
| 6,206,832 B1 | 3/2001 | Downey et al. | |
| 6,231,570 B1 | 5/2001 | Tu et al. | |
| 6,264,679 B1 | 7/2001 | Keller et al. | |
| 6,270,494 B1 | 8/2001 | Kovalcheck et al. | |
| 6,287,326 B1 | 9/2001 | Pecor | |
| 6,306,129 B1 | 10/2001 | Little et al. | |
| 6,315,713 B1 | 11/2001 | Takada | |
| 6,330,478 B1 | 12/2001 | Lee et al. | |
| 6,383,144 B1 | 5/2002 | Mooney et al. | |
| 6,383,181 B1 | 5/2002 | Johnston et al. | |
| 6,419,462 B1 | 7/2002 | Horie et al. | |
| 6,468,268 B1 | 10/2002 | Abboud et al. | |
| 6,505,629 B1 | 1/2003 | Mikus et al. | |
| 6,613,044 B2 | 9/2003 | Carl | |
| 6,652,515 B1 * | 11/2003 | Maguire et al. | 606/41 |
| 6,706,037 B2 | 3/2004 | Zvuloni et al. | |
| 6,770,070 B1 * | 8/2004 | Balbierz | 606/41 |
| 7,150,743 B2 | 12/2006 | Zvuloni et al. | |
| 2002/0040220 A1 | 4/2002 | Zvuloni et al. | |
| 2002/0049436 A1 | 4/2002 | Zvuloni et al. | |
| 2002/0188287 A1 * | 12/2002 | Zvuloni et al. | 606/21 |
| 2003/0032896 A1 | 2/2003 | Bosley, Jr. et al. | |
| 2003/0032936 A1 | 2/2003 | Lederman | |
| 2003/0060820 A1 * | 3/2003 | Maguire et al. | 606/41 |
| 2003/0181896 A1 * | 9/2003 | Zvuloni et al. | 606/20 |
| 2004/0049177 A1 | 3/2004 | Zvuloni et al. | |
| 2004/0059328 A1 | 3/2004 | Daniel et al. | |
| 2004/0138656 A1 | 7/2004 | Francischelli et al. | |
| 2004/0143252 A1 | 7/2004 | Hurst | |
| 2004/0204705 A1 * | 10/2004 | Lafontaine | 606/21 |
| 2004/0267248 A1 | 12/2004 | Duong et al. | |
| 2005/0085691 A1 | 4/2005 | Nakao | |
| 2005/0224085 A1 | 10/2005 | Zvuloni | |
| 2005/0251124 A1 | 11/2005 | Zvuloni et al. | |
| 2007/0088247 A1 | 4/2007 | Bliweis et al. | |
| 2007/0167938 A1 | 7/2007 | Zvuloni et al. | |
| 2008/0045934 A1 | 2/2008 | Schechter et al. | |
| 2008/0051774 A1 | 2/2008 | Ofir et al. | |
| 2008/0051776 A1 | 2/2008 | Bliweis et al. | |
| 2008/0300586 A1 | 12/2008 | Zvuloni | |

FOREIGN PATENT DOCUMENTS

| | | |
|---|---|---|
| DE | 19540731 | 5/1997 |
| DE | 10024660 | 11/2000 |
| EP | 0608927 | 8/1994 |
| EP | 0624347 | 11/1994 |
| EP | 0651308 | 5/1995 |
| EP | 0947172 | 10/1999 |
| EP | 1048272 | 11/2000 |
| JP | 07-110175 | 4/1995 |
| JP | 07-127939 | 5/1995 |
| WO | WO 96/37158 | 11/1996 |
| WO | WO 98/00341 | 1/1998 |
| WO | WO 98/14111 | 4/1998 |
| WO | WO 98/52480 | 11/1998 |
| WO | WO 99/04211 | 1/1999 |
| WO | WO 99/56639 | 11/1999 |
| WO | WO 99/63881 | 12/1999 |
| WO | WO 00/22996 | 4/2000 |
| WO | WO 02/34106 | 5/2002 |
| WO | WO 2004/043272 | 5/2004 |
| WO | WO 2005/018428 | 3/2005 |
| WO | WO 2007/069248 | 6/2007 |
| WO | WO 2007/086056 | 8/2007 |

OTHER PUBLICATIONS

Communication Pursuant to Article 96(2) EPC Dated Jul. 19, 2004 From the European Patent Office Re.: Application No. 00650043.3.
Communication Relating to the Results of the Partial International Search Dated Jul. 3, 2007 From the International Searching Authority Re.: Application No. PCT/IL2007/000091.
International Preliminary Report on Patentability Dated Aug. 7, 2008 From the International Bureau of WIPO Re.: Application No. PCT/IL2007/000091.
Official Action Dated Dec. 8, 2005 From the US Patent and Trademark Office Re.: U.S. Appl. No. 10/151,310.
Official Action Dated Feb. 8, 2007 From the US Patent and Trademark Office Re.: U.S. Appl. No. 11/185,699.
Official Action Dated Oct. 18, 2004 From the US Patent and Trademark Office Re.: U.S. Appl. No. 09/987,689.
Official Action Dated Jan. 26, 2005 From the US Patent and Trademark Office Re.: U.S. Appl. No. 10/151,310.
Response Dated Nov. 2, 2004 to Official Action of Jun. 3, 2004 From the US Patent and Trademark Office Re.: U.S. Appl. No. 10/151,310.
Communication Relating to the Results of the Partial International Search Dated Jul. 2, 2007 From the International Searching Authority Re.: Application No. PCT/IL2006/001432.
Response Dated Feb. 17, 2010 to Communication Pursuant to Article 94(3) EPC of Aug. 19, 2009 From the European Patent Office Re.: Application No. 06821642.3.
Response Dated Feb. 22, 2010 to Communication Pursuant to Article 94(3) EPC of Aug. 19, 2009 From the European Patent Office Re.: Application No. 07706034.1.
Communication Pursuant to Article 94(3) EPC Dated Aug. 19, 2009 From the European Patent Office Re.: Application No. 06821642.3.
Communication Pursuant to Article 94(3) EPC Dated Aug. 19, 2009 From the European Patent Office Re.: Application No. 07706034.1.
Official Action Dated Sep. 15, 2009 From the US Patent and Trademark Office Re.: U.S. Appl. No. 11/637,095.
Official Action Dated Nov. 30, 2009 From the US Patent and Trademark Office Re.: U.S. Appl. No. 11/637,095.
Response Dated Oct. 15, 2009 to Official Action of Sep. 15, 2009 From the US Patent and Trademark Office Re.: U.S. Appl. No. 11/637,095.

* cited by examiner

MULTIPLE CRYOPROBE DELIVERY APPARATUS

RELATED APPLICATIONS

This application is a continuation of pending U.S. patent application Ser. No. 10/660,478 filed on Sep. 12, 2003, which is a continuation of U.S. patent application Ser. No. 09/860,486 filed on May 21, 2001, now U.S. Pat. No. 6,706,037, which claims the benefit of U.S. Provisional Patent Application No. 60/242,455 filed Oct. 24, 2000, now expired. The contents of the above applications are all incorporated herein by reference.

FIELD AND BACKGROUND OF THE INVENTION

The present invention relates to an apparatus and method of cryoablation, and more particularly for cryoablation using multiple probes introduced into the body of a patient through a common introducer, so as to perform cryoablation of a particular volume of tissue while minimizing damage to adjacent healthy tissues.

A variety of medical conditions are preferentially treated by ablation of tissues within the body. Classically, ablation was performed using invasive surgical procedures requiring cutting or destroying tissues between the exterior of the body and the particular site whose ablation is desired. More recently, less invasive procedures have been developed, which bring about the destruction of selected tissues using a probe or probes which penetrate to the area to be operated, and destroy the selected tissue by transferring energy to those tissues; RF energy, light (laser) energy, microwave energy, and high-frequency ultra-sound energy are among the forms which have been used. However all such methods have the common disadvantage that while transferring energy to the tissues whose destruction is intended, they tend also to transfer energy, through conduction, convection, and other natural processes, to nearby healthy tissues as well. All such energy transfer methods ultimately result in heat release, causing complications and adverse effects. Noticeable pain results, the functioning of nearby healthy tissues is impaired, and the healthy tissues are often damaged or destroyed. Moreover, in some cases tissues exposed to thermal energy or other forms of energy that raise their temperatures secrete substances that may be toxic to adjacent healthy tissues.

In contrast, cryoablation provides a number of important advantages over other ablation techniques. Cryoablation provides better control of the ablated volume than is attainable using other procedures. Moreover, real-time imaging during cryoablation, using ultrasound and MRI techniques, is helpful and straightforward, since the frozen tissue is clearly seen under these imaging techniques. Also, cryoablation, unlike heat radiation techniques, allows for repeatable and/or complementary treatment of the affected area. Cryoablation is considered to cause less pain to the patients. Some scientific evidence supports the conclusion that there is less morbidity and less risk of mortality as a result of cryoablation procedure compared to other minimally invasive and traditional techniques. For these and other reasons, cryoablation has recently become a popular method for certain types of minimally invasive ablation procedures. Examples include the treatment of prostate malignant tumors and of benign prostate hyperplasia (BPH), and the creation of trans-myocardial channels to effect trans-myocardial revascularization.

Yet, cryoablation procedures also have an inherent disadvantage. Cryoprobes when activated typically form at their tip what is know in the art as an "ice ball", a volume which is frozen by exposure to the low temperatures developed by the cryoprobe. Unfortunately, the radius of the volume in which total destruction of tissues is achieved (such destruction of tissues being the purpose of the operation) is typically only half of the radius of the volume within which tissues are more or less severely damaged. Since the volume of a sphere is proportional to the cube of the radius, the volume of total cell destruction, for a particular ice-ball, will typically be only the order of one-eighth of the volume of the area that is frozen during the operation and more or less severely damaged. The disadvantage is clear: if a single ice-ball is used to destroy a selected volume, and the ice-ball is large enough to ensure the complete destruction of that volume (which complete destruction would be desired in the case of a malignancy, for example), then a surrounding volume approximately seven times larger will be more or less severely damaged. That surrounding volume will typically include much healthy tissue that would preferably be left healthy and intact. In the case of ablation of the prostate, for example, freezing of surrounding tissues using simple cryosurgical techniques will typically damage or destroy, and create temporary or permanent impairment of the function of, the prostatic urethra, the anus, and various bundles of nerves in the prostatic area.

One method of solving this problem is taught by U.S. Pat. No. 6,142,991 to Schatzberger, teaching the use of a series of ice-balls of small dimensions, such as can be created by a two-dimensional array of cryoprobes whose depth of penetration can be measured and controlled, so as to achieve accurate three-dimensional placement of a plurality of ice-balls, in a manner that conforms to the dimensions and form and placement of the lesion to be destroyed. In other words, Schatzberger's apparatus defines a volume of controllable form and dimension, for cryoablation. The ice-balls created by the apparatus are each of small dimensions, and they are placed so as to be contiguous to one another or to overlap each other. This arrangement results in a reduction of the amount of tissue that is damaged but not destroyed, and permits more accurate definition of the exact form and dimensions of the ablated tissue.

The mechanism described by Schatzberger is not, however, well adapted to every application of cryoablation. It is relatively complex, and requires penetration of the affected area by a multiplicity of individually introduced and individually handled cryoprobes. It could not be used, for example, in the context of cryoablating benign prostate hyperplasia (BPH) through the urethra, a relatively non-invasive treatment method described in U.S. patent application Ser. No. 09/301,576, filed Apr. 29, 1999, and incorporated herein by reference. That procedure requires an apparatus which is both simpler and more compact than that described by Schatzberger, in that the procedure requires the operating portion of the cryogenic apparatus to be introduced to the area of the lesion by means of a cystoscope, in order to reduce reducing trauma to healthy tissue.

Thus there is a widely recognized need for, and it would be highly advantageous to have, a method and apparatus for cryoablation that provides for the destruction of a defined volume of tissue, yet which minimizes damage to adjacent tissues. It would be further advantageous to have a method of cryoablation using an apparatus that creates such an extended volume of cryoablation yet is contained within a single introducer. It would be yet further advantageous to have such an introducer which could be introduced through an operating channel of a catheter or cystoscope, enabling it to reach the proximity of the region to be treated with a minimum of trauma to intervening tissues.

Referring now to another aspect of prior art, two-stage heating and cooling has successfully been used in surgical cryoablation systems, particularly in two-stage cooling of a high-pressure gas used to achieve cryogenic temperatures using Joule-Thomson heat exchangers. Two-stage cooling presents the advantages of more rapid and more efficient cooling than would be possible in a single Joule-Thomson cooling stage. In U.S. Pat. No. 5,993,444 to Ammar a cryogenic probe utilizes two stages of Joule-Thomson cooling to achieve low temperatures at the operating end of the probe. Ammar describes, however, a single probe so cooled.

Schatzberger, in the patent previously cited, describes two-stage cooling in a multi-probe system. In FIG. 6a Schatzberger teaches a plurality of cryosurgical probes connected by flexible connectors to a common housing which includes a pre-cooling element for pre-cooling the high-pressure gas flowing to the probes, this element being preferably a Joule-Thomson heat exchanger used as a cooler. Schatzberger's system thus utilizes two-stage cooling, with pre-cooling taking place extracorporeally in the housing and a second cooling stage taking place in each individual cryoprobe. Furthermore, the mechanism Schatzberger describes has the disadvantage that the pre-cooled gases must be transported a considerable distance between the housing and the probe, and the conduit connecting the probe to the housing, which must remain flexible, must also be thermally insulated.

Consequently, it would be further advantageous to have a cryoablation apparatus and method which enables the pre-cooling of a plurality of cryoprobes within a single introducer, such that the pre-cooling stage of a two-stage Joule-Thomson heat exchange process can take place in close proximity to a second stage of cooling which takes place within the individual cryoprobes.

SUMMARY OF THE INVENTION

According to one aspect of the present invention there is provided a cryosurgery apparatus comprising an introducer having a hollow and a distal portion, the distal portion being sufficiently sharp so as to penetrate into a body, the hollow of the introducer being designed and constructed for containing a plurality of cryoprobes each of the cryoprobes being for effecting cryoablation, such that each of the plurality of cryoprobes is deployable through the distal portion of the introducer when the distal portion is positioned with respect to a tissue to be cryoablated.

According to further features in preferred embodiments of the invention described below, the introducer comprises a cooling device designed and constructed to cool the hollow of the introducer, and a heating device designed and constructed to heat the hollow. The cooling device and heating device may be a combined heating/cooling device, such as a Joule-Thomson heat exchanger.

According to still further features in the described preferred embodiments, the introducer includes a heating and cooling device for pre-heating and pre-cooling gasses which are passed through at least a portion of the introducer and are subsequently delivered to at least one of the cryoprobes. The heating and cooling device will preferably be a Joule-Thomson heat exchanger. The introducer will further comprise a heat-exchanging configuration for exchanging heat between a gas passed to at least one of a plurality of cryoprobes and the heating and cooling device. A thermal sensor, such as a thermocouple, will preferably be used to monitor temperature in the hollow.

According to still further features in the described preferred embodiments, the introducer is designed and constructed to be coupled to at least one high-pressure gas source, the gas source being coupleable to a Joule-Thomson heat exchanger having a Joule-Thomson orifice in the introducer. The gas source may be a source of at least one gas selected from a group consisting of high-pressure argon, high-pressure nitrogen, high-pressure air, high-pressure krypton, high-pressure $CF_4$, high-pressure $N_2O$, and high-pressure carbon dioxide. The gas source may also be a source of high-pressure helium. The introducer is designed and constructed so as to facilitate exchange of heat between two temperature states of gas from the high-pressure gas source, gas in a first state being at a first temperature prior to passing through the Joule-Thomson orifice, and gas in a second state being at a second temperature subsequent to passing through the Joule-Thomson orifice.

According to still further features in the described preferred embodiments, the introducer is designed and constructed to be coupled both to a first gas source and to a second gas source. The gas provided by the first gas source is cooled by expansion and may liquefy when passing through a Joule-Thomson orifice. The gas provided by the second gas source has an inversion temperature lower than the temperature obtained by liquefaction of gas provided by the first gas source. The apparatus further comprises control elements for regulating a flow of gas from the first gas source and the second gas source.

According to still further features in the described preferred embodiments, the introducer further comprises a plurality of cryoprobes contained therein. The distal end of the introducer is formed with a plurality of openings for deployment therethrough of the cryoprobes. Preferably, at least one of the pluralities of cryoprobes is coolable, and the coolable cryoprobe is also heatable. Preferably, the cryoprobes comprise a Joule-Thomson heat exchanger having a Joule-Thomson orifice, for heating and cooling the cryoprobes.

According to still further features in the described preferred embodiments, the hollow of the introducer is partitioned into a plurality of longitudinal compartments; each of the plurality of longitudinal compartments is designed and constructed for containing at least one of the pluralities of cryoprobes.

According to still further features in the described preferred embodiments, the introducer comprises thermal insulation designed and constructed so as to hinder the passage of heat between the hollow of the introducer and tissues of the body, when the introducer is positioned within the body.

According to still further features in the described preferred embodiments, the introducer comprises a heat-exchanging configuration. The heat-exchanging configuration may include a porous matrix, which may include a conduit tunneling through at least a portion of the porous matrix, and which may include a spiral conduit integrated with the porous matrix.

According to still further features in the described preferred embodiments, the cryoprobes preferably comprise a distal operating head which includes a thermally conductive outer sheath having a closed distal end and a chamber formed within the sheath, the operating head being adapted to be inserted into a body and to effect cryoablation thereat. The chamber serves as a reservoir for housing a fluid in contact with at least a portion of the outer sheath of the distal operating head.

According to still further features in the described preferred embodiments, the cryoprobes are designed and constructed coupleable to at least one high-pressure gas source, and preferably to a first gas source and also to a second gas source. The first gas source provides a first gas, which is cooled by expansion and may liquefy when passed through the Joule-Thomson orifice. A second gas from said second gas source has an inversion temperature lower than a temperature obtained by liquefaction of said first gas.

According to still further features in the described preferred embodiments, the cryoprobes are designed and constructed so that gas from the high-pressure gas source, while in a first temperature state prior to passing through a Joule-Thomson orifice, exchanges heat with gas from the high-pressure gas source which is in a second temperature state subsequent to having passed through the Joule-Thomson orifice. Control elements are provided for regulating the flow of gas from the first gas source and from the second gas source.

According to still further features in the described preferred embodiments, at least one of the pluralities of cryoprobes is designed and constructed so as to expand laterally away from the introducer when deployed. Preferably, at least some of the plurality of cryoprobes are designed and constructed to advance, during deployment, in a plurality of different directions. Also preferably, each cryoprobe deploys from the introducer according to a predetermined path, and the plurality of cryoprobes are designed and constructed to be deployed laterally away from the introducer to form a predetermined arrangement of deployed cryoprobes. The plurality of cryoprobes, designed and constructed to advance from within the introducer and deploy in a lateral direction away from a periphery of the introducer, thereby define a three-dimensional cryoablation volume, which may be of predetermined shape.

According to still further features in the described preferred embodiments, each cryoprobe is retractable and advanceable in and out of the introducer. An advancing and retracting member may be operably coupled to one or more cryoprobe of the plurality of cryoprobes.

According to still further features in the described preferred embodiments, at least one cryoprobe of the plurality of cryoprobes has a sharp distal end.

According to still further features in the described preferred embodiments, at least one cryoprobe of the plurality of cryoprobes has a blunt distal end.

According to still further features in the described preferred embodiments, at least one of the pluralities of cryoprobes comprises a Joule-Thomson heat exchanger. Preferably, the Joule-Thomson heat exchanger is coupled to a tube through which gasses enter the cryoprobe, the tube has an orifice located at a distal end of the tube, the orifice opens into a sheath which includes a thermally conductive material designed and constructed to conduct heat when the cryoprobe is in contact with a body tissue to be cryoablated. Preferably, the Joule-Thomson heat exchanger comprises a coiled tube housed within the thermally conductive sheath, and the Joule-Thomson heat exchanger further comprises a gas supply line on its proximal end and a gas outlet on its distal end, the outlet being in fluid communication with a chamber.

According to still further features in the described preferred embodiments, at least one of the pluralities of cryoprobes comprises a heat-exchanging configuration. The heat exchanging configuration may include a porous matrix, which may include a conduit tunneling through at least a portion of the porous matrix, and which may include a spiral conduit integrated with the porous matrix.

According to still further features in the described preferred embodiments, at least one of the pluralities of cryoprobes comprises a thermal sensor for monitoring local temperature conditions in areas in close proximity to the sensor. Preferably, at least one of the pluralities of cryoprobes further comprises a feedback control system coupled to a gas source and to the thermal sensor; the feedback system is responsive to a detected characteristic from the thermal sensor and serves for controlling a rate of delivery of gas from the gas source to the cryoprobe. The thermal sensor is preferably positioned at the distal end of the cryoprobe, and may include a thermocouple.

According to still further features in the described preferred embodiments, at least one of said plurality of cryoprobes comprises a shape memory alloy material. The shape memory alloy material displays stress induced martensite behavior at a deployed position. The shape memory alloy material is in a non-stress induced martensite state when said cryoprobe is positioned in the introducer prior to deployment of the cryoprobe outside the introducer. Preferably the shape memory alloy material is an alloy of nickel titanium.

According to still further features in the described preferred embodiments, a cross section of each of said plurality of cryoprobes is between 0.3 mm and 3 mm.

According to another aspect of the present invention there is provided a method of cryosurgery comprising: (a) introducing into a body of a patient an introducer having a hollow and a distal portion being sufficiently sharp so as to penetrate into the body of the patient, the hollow of the introducer containing a plurality of cryoprobes each being capable of effecting cryoablation, each of the plurality of cryoprobes is deployable through the distal portion of the introducer; (b) deploying at least one of the plurality of cryoprobes; and (c) cryoablating a tissue of the patient with at least one of the plurality of cryoprobes.

According to further features in preferred embodiments of the invention described below, the step of cryoablating a tissue of the patient with at least one of the plurality of cryoprobes is accomplished by supplying a high-pressure gas to at least one of the plurality of cryoprobes, and cooling the cryoprobe by passing the gas through a Joule-Thomson orifice in a Joule-Thomson heat exchanger within the cryoprobe.

According to still further features in the described preferred embodiments, the cryosurgery method further comprises the step of cooling the gas within the body of the introducer prior to passing the gas through a Joule-Thomson orifice in the Joule-Thomson heat exchanger within the cryoprobe.

According to still further features in the described preferred embodiments the cryosurgery method further comprises heating at least one of the pluralities of cryoprobes prior to removing the cryoprobe from a site of cryoablating of a tissue of the patient.

According to still further features in the described preferred embodiments the cryosurgery method further comprises the step of deploying at least several cryoprobes, thereby defining a three dimensional cryoablation volume, and cryoablating, the volume so defined. Preferably, an imaging device is used to position at least one of the plurality of cryoprobes with respect to a tissue to be cryoablated. Preferably, the imaging device is selected from the group consisting of an ultrasound device, a computerized tomography (CT) device, a closed magnetic resonance imaging (MRI) device, an open magnetic resonance imaging (MRI) device, a fluoroscope device and an X-ray device.

According to still further features in the described preferred embodiments the cryosurgery method further comprises the step of inducing fast cyclical temperature changes in a deployed cryoprobe, such that a temperature of said probe alternates rapidly between a temperature of approximately 0° C. and a temperature below −40° C.

The present invention successfully addresses the shortcomings of the presently known configurations by providing a method and apparatus for cryoablation that provides for the destruction of a defined volume of tissue, yet minimizes damage to adjacent tissues.

The present invention further successfully addresses the shortcomings of the presently known configurations by providing a method of cryoablation using an apparatus that creates an extended volume of cryoablation yet is contained within a single introducer.

The present invention still further successfully addresses the shortcomings of the presently known configurations by providing an apparatus having an introducer which could be introduced through an operating channel of a catheter or cystoscope, enabling it to reach the proximity of the region to be treated with a minimum of trauma to intervening tissues.

The present invention yet further successfully addresses the shortcomings of the presently known configurations by providing a cryoablation apparatus and method which enables the pre-cooling of a plurality of cryoprobes within a single introducer, such that the pre-cooling stage of a two-stage Joule-Thomson heat exchange process can take place in close proximity to a second stage of cooling which takes place within the individual cryoprobes.

Implementation of the method and the apparatus of the present invention involves performing or completing selected tasks or steps manually, automatically, or a combination thereof Moreover, according to actual instrumentation and equipment of preferred embodiments of the method and apparatus of the present invention, several selected steps could be implemented by hardware or by software on any operating system of any firmware or a combination thereof. For example, as hardware, control of selected steps of the invention could be implemented as a chip or a circuit. As software, control of selected steps of the invention could be implemented as a plurality of software instructions being executed by a computer using any suitable operating system. In any case, selected steps of the method of the invention could be described as being controlled by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a cryosurgical apparatus and method of cryosurgery. Specifically, the present invention can be used to effect cryoablation of selected tissues of a patient. In particular, the apparatus and method of the invention provide for the cryoablation of tissues with a minimum of damage to healthy tissues adjacent to the tissues to be cryoablated.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice through which gas passes from the first, higher pressure, region of the device to the second, lower pressure, region of the device. It may further include a heat-exchanging configuration, for example a heat-exchanging configuration used to cool gasses from the first region of the device, prior to their expansion into the second region of the device. As is described hereinbelow, the expansion of certain gasses (referred to herein as "cooling gases") in a Joule-Thomson heat exchanger, when passing from a region of higher pressure to a region of lower pressure, causes these gasses to cool and may cause them to liquefy, creating a cryogenic pool of liquefied gas. This process cools the Joule-Thomson heat exchanger itself, and also cools any thermally conductive materials in contact therewith. As further described hereinbelow, the expansion of certain other gasses (referred to herein as "heating gasses") in a Joule Thompson heat exchanger causes the gas to heat, thereby heating the Joule-Thomson heat exchanger itself and also heating any thermally conductive materials in contact therewith.

The principles and operation of a cryosurgical apparatus and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cryoablation is typically performed in cases where a tissue of a patient has been diagnosed as undergoing inappropriate, e.g., malignant or benign, growth or development. Cryoablation might be used, for example, in the case of a malignant tumor, or in the case of a non-malignant mass compressing healthy tissues, thereby disturbing the normal functioning thereof. The operation might typically be performed in tissues of the prostate, kidney, lung, liver, bone, or breast, or in other tissues. In these and similar cases, cryoablation may be used to destroy the offending tissues.

Figure 1:
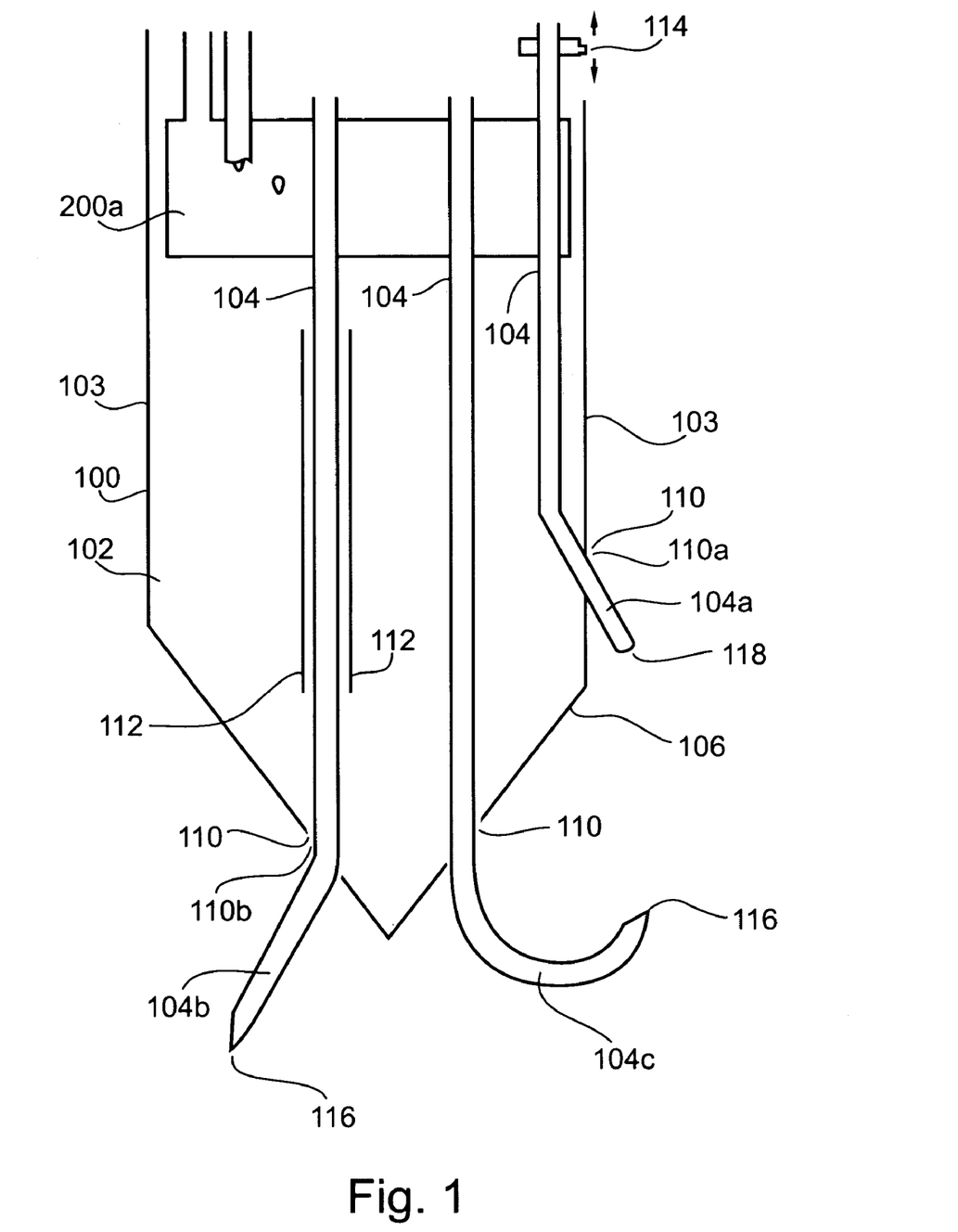
FIG. 1 is an introducer for introducing a plurality of cryoprobes into a body for effecting cryoablation, according to the present invention.

Referring now to the drawings, FIG. 1 illustrates the basic principle of the invention herein described. An introducer 100 in accordance with the teachings of the present invention, is designed and constructed so as to be sufficiently sharp, so as to easily penetrate through body tissue, inflicting minimal damage to nearby tissues. Introducer 100 has a hollow 102. Hollow 102 is designed and constructed for containing a plurality of cryoprobes 104. Each of cryoprobes 104 is capable of being cooled to a low temperature, say −60 to −120° C., or preferably less, and is capable of freezing tissues, for effecting cryoablation.

A distal portion 106 of introducer 100 is formed with a plurality of openings 110. As is further detailed hereinbelow, openings 110 of introducer 100 serve for deployment therethrough of a plurality of cryoprobes 104. Each of cryoprobes 104 contained within introducer 100 is deployable outside introducer 100, and in the deployed state is capable of effecting cryoablation. Hollow 102 may optionally be partitioned into a plurality of longitudinal compartments 112, each compartment 112 is designed and constructed for containing at least one, preferably one, cryoprobe 104. Hollow 102 of introducer 100 optionally includes a Joule-Thomson heat exchanger 200a (described in detail hereinbelow) for pre-heating and pre-cooling at least a portion of hollow 102, thereby cooling gasses used for heating and cooling of cryoprobes 104. External sheath 103 of introducer 100 may include thermally insulating material(s), so as to prevent heat exchange between hollow 102 of introducer 100 and tissues of the body, when introducer 100 is introduced into a body.

The mode of operation of the cryosurgery apparatus and method of the present invention involves introducing introducer 100 with its plurality of cryoprobes 104 contained within hollow 102 into the body of a patient, then, deploying through openings 110 present at distal portion 106 of introducer 100 at least one of cryoprobes 104, and cooling the deployed cryoprobe or cryoprobes 104 to perform cryoablation.

The image of introducer 100 has been expanded in FIG. 1, so as to enhance visibility of details, yet introducer 100 is preferably thin in construction, so as to permit its introduction into the body in a manner that minimizes damage to tissues present along its penetration path, leading to the intended site of cryoablation. Preferably a cross-section of sheath 103 will not exceed 6 mm. In a presently preferred mode of operation, cryoprobes 104 are initially positioned within the introducer (i.e., retracted) so that they do not hinder the penetration of the introducer into the body of the patient. Each cryoprobe 104 is designed and constructed deployable through openings 110 present at distal portion 106 of introducer 100, when distal portion 106 is appropriately positioned with respect to a tissue to be cryoablated. An optional deploying and retracting member 114, shown in FIG. 1 operably coupled to a cryoprobe 104a, may be operably coupled to some or all of cryoprobes 104. For most applications it will be convenient for cryoprobes 104 to be provided with sharp distal end 116 to aid in penetration of tissues during deployment, yet under some circumstances a cryoprobe 104 with a blunt or rounded distal end 118 may preferably be used.

In a preferred embodiment each of cryoprobes 104 has a cross section of between 0.3 mm and 3 mm. In their undeployed, retracted, state, cryoprobes 104 will fit in the space made available for them within hollow 102 of introducer 100. This allows introducer 100 to penetrate the body of a patient with little hindrance. Once at the desired cryoablation site, some or all of cryoprobes 104 are deployed beyond introducer 100, penetrating further into the body's tissues, at which time cryoablation is performed.

In one preferred embodiment of the invention, cryoprobes 104 are designed and constructed to advance, during deployment, in a plurality of different directions. Generally, some of the cryoprobes are designed and constructed so as to expand laterally away from the introducer when deployed. As cryoprobes 104 so designed and constructed advance from within introducer 100 and deploy in a lateral direction away from the periphery of introducer 100, they thereby define a three-dimensional cryoablation volume.

In a preferred embodiment of the present invention, cryoprobes 104 are partly constructed of shape memory alloy material, such as nitinol, a nickel titanium alloy. In typical use, shape memory alloy material used in cryoprobe 104 displays stress induced martensite behavior when cryoprobe 104 is at its deployed position. Also in typical use, shape memory alloy material used in cryoprobe 104 is in a non-stress induced martensite state when cryoprobe 104 is positioned within introducer 100.

The use of shape memory material in the construction of cryoprobes 104 results in each cryoprobe being characterized by a particular shape and hence a particular position with respect to the position of introducer 100, at the time of its deployment within the body. Cryoprobes 104 may be deployed substantially to one side of introducer 100, for cryoablation of a volume substantially located alongside introducer 100. Alternatively, introducer 100 may be introduced into a lesion, and cryoprobes 104 may be deployed substantially around introducer 100, for cryoablation of a volume surrounding the position of introducer 100. Generally, deployment of cryoprobes 104 creates a shaped volume of deployed cryoprobes, which may be a predefined shaped volume within the body. Deployed cryoprobes 104 are then cooled so as to perform cryoablation, resulting in a shaped volume of cryoablation.

It is a major advantage of the method of the present invention that a surgeon performing a cryoablation can cause the shape and position of the cryoablation volume substantially to conform to the shape and position of the tissues the surgeon desires to cryoablate. The method of the present invention permits cryoablation of exactly defined, preselected volumes.

FIG. 1 provides examples of a manner in which cryoprobes deploy from introducer 100, each according to a predetermined path, under the influence of shape memory alloy. Cryoprobe 104a, for example, deploys laterally, from a side opening 110a formed in distal portion 106 of introducer 100. Cryoprobe 104b, on the other hand, deploys in a largely forward direction, from a forward opening 110b formed in distal portion 106 of introducer 100. Both cryoprobe 104a and cryoprobe 104b illustrate deployment of a cryoprobe 104 along a predetermined path characterized by being at a specific angle with respect to introducer 100. In a slightly different example, shape memory alloy is used to cause a cryoprobe 104c to deploy according to a predetermined path characterized by a particular radius of curvature. Cryoprobes 104a, 104b, and 104c illustrate the general principle that each of a plurality of cryoprobes 104 may be prepared for deployment and may be deployed each according to a predetermined path, such that the combination of deployed cryoprobes 104 creates a predetermined arrangement of deployed cryoprobes 104, which together define a specific shape at a specific position in the vicinity of introducer 100. In practice, the arrangement of cryoprobes 104 within introducer 100 may be preselected in accordance with a predefined cryoablation task.

When deployed cryoprobes 104 are cooled to cryoablation temperatures, e.g., −60° to −160° C., preferably −80° to −120° C., the cooled volumes provided by each of the deployed cryoprobes 104 combine to produce a shaped cooled volume within which cryoablation is effected. This method of arranging and deploying the cryoprobes thus creates a three-dimensional cryoablation volume of a predetermined size and shape.

According to a preferred method of operation, diagnostic procedures such as medical imaging and computer simulation are used in advance of the cryosurgery operation to approximately determine the position and shape of the tissues to be cryoablated and a configuration of cryoprobes 104 which, when deployed, will define a similar shape. Cryoprobes 104 are then selected, prepared, and placed within introducer 100 in such a manner that when cryoprobes 104 are deployed they will approximately form a predetermined shape which appropriately conforms to the diagnosed shape of the tissues to be cryoablated.

In a currently preferred method of operation according to the present invention, medical imaging equipment such as X-ray, fluoroscope, computerized tomography (CT), ultrasound, MRI (open MRI in particular), or other forms of imaging equipment is used during the operation to guide the introduction of introducer 100 into the body of a patient, to guide the placement of introducer 100 in the vicinity of the site intended for cryoablation, and to guide the deployment of cryoprobes 104 at that site, thereby ensuring that the actual shape and placement of deployed cryoprobes 104 appropriately corresponds to the placement and shape of the tissues to be cryoablated. Cooling of the deployed cryoprobes 104 is then used to cryoablate a volume of tissue approximately corresponding to the predetermined shape intended to be cryoablated. This method has the advantage of minimizing the destructive effect of the cryoablation procedure on healthy tissues in the vicinity of the cryoablated tissues.

Figure 2:
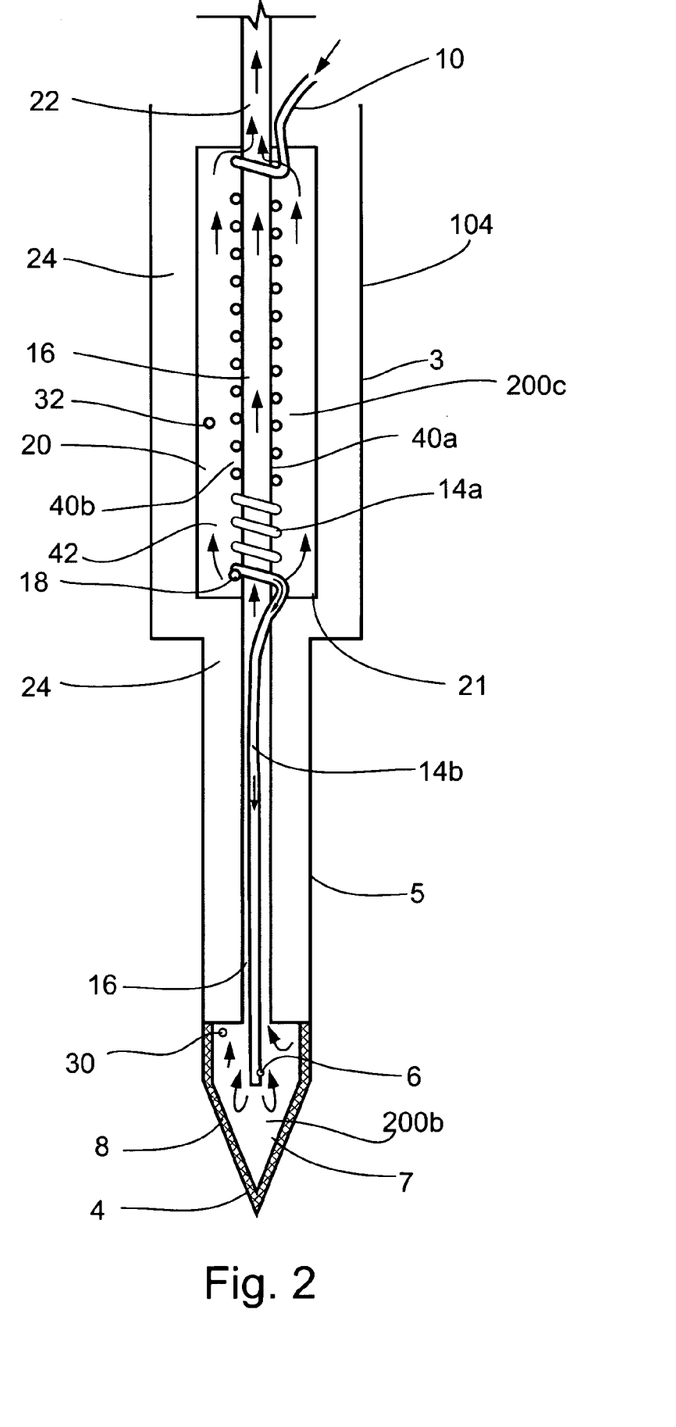
FIG. 2 is a is a schematic side view, partially in longitudinal cross-section, of an exemplary cryoprobe according to the present invention.

FIG. 2 illustrates an individual cryoprobe 104 according to a preferred embodiment of the present invention. Cryoprobe 104 preferably includes elongated housing 3 having a distal operating head 4 for penetrating through tissues of a patient during deployment.

Distal operating head 4 is connected to elongated housing 3 by means of an elongated member 5 substantially thin in cross section for allowing deployment into the tissues of a body. Elongated housing 3, elongated member 5, and other elements of cryoprobe 104 may include shape memory alloy, as described above.

As shown in FIG. 2, cryoprobe 104 preferably includes a first passageway 10 extending along its length for providing gas of high-pressure to a Joule-Thomson heat exchanger 200b located at distal operating head 4, and a second passageway 16 for evacuating gas from the operating head to atmosphere. First passageway 10 is preferably in the form of a substantially thin tubular element extending along elongated housing 3, elongated member 5, and a portion of operating head 4. As shown in the figure, the portion of first passageway 10 extending along elongated housing 3 is preferably in the form of a spiral tube 14a wrapped around second passageway 16, thereby constituting a heat-exchanging configuration 40a for exchanging heat between spiral tube 14a and second passageway 16. The portion of first passageway 10 extending along elongated member 5 and portion of operating head 4 is preferably in the form of a straight tube 14b received within second passageway 16. Further as shown in the figure, tube 14b preferably penetrates into second passageway 16 substantially adjacent the connection of elongated member 5 and housing 3.

Further, elongated housing 3 preferably includes a third passageway 20 enclosing first and second passageways 10 and 16, which third passageway forming a heat-exchanging configuration 40b in the form of a heat exchanging chamber for precooling or preheating gas flowing within spiral tube 14a before it arrives to operating head 4. Third passageway 20 preferably merges with second passageway 16 at the upper end of elongated housing 3 to form a common passageway 22 for releasing gas to atmosphere.

In an alternative construction, heat exchanging configuration 40b may be formed as a porous matrix 42 filling or partially filling passageway 20, with spiral tube 14a being formed as a spiral conduit integrated into porous matrix 42 and second passageway 16 being formed as a straight conduit tunnelling through porous matrix 42.

As shown in the figures, the various passageways of the device are enclosed by an insulating chamber 24 extending along housing 3 and elongated member 5.

Preferably, a device according to the present invention provides effective cooling or heating by using Joule-Thomson heat exchangers. Thus, first passageway 10 preferably includes a plurality of orifices for passage of high-pressure gas therethrough so as to cool or heat selective portions of the device, depending on the type of gas used. Gases that may be used for cooling include argon, nitrogen, air, krypton, $CF_4$, xenon, $N_2O$, or any mixture of gases, and are referred to herein as "cooling gasses". High pressure cooling gasses are cooled by expansion when passing through a Joule-Thomson orifice, thereby providing their cooling effect. Gases that may be used for heating include helium or any mixture of gases, and are referred to herein as "heating gasses." Heating gasses have an inversion temperature lower than temperature obtained by liquefaction of cooling gas.

According to the embodiment shown in FIG. 2, a primary Joule-Thomson heat exchanger 200b is located-at distal operating head 4, which heat exchanger including: an orifice 6 located preferably at the end of straight tube 14b, and a chamber 7 defined by the inner walls of head 4. When a high-pressure cooling gas such as argon passes through orifice 6 it expands, causing it to cool and in some cases to liquify so as to form a cryogenic pool within chamber 7 of operating head 4. The cooled expanded gas, and the cryogenic pool of liquefied gas which may form, effectively cool outer sheath 8 of operating head 4. Outer sheath 8 is preferably made of a heat conducting material such as metal for effectively freezing body tissue so as to produce the desired cryoablation effect. When a high-pressure heating gas such as helium expands through orifice 6 it heats chamber 7 of operating head 4, thereby heating outer sheath 8 of the operating head. Such heating of the operating head may be used for preventing sticking of the device to the tissue being cryoablated.

According to a preferred embodiment of the present invention cryoprobe 104 preferably includes a plurality of Joule-Thomson heat exchangers 200c for effectively precooling or preheating the gas flowing within first passageway 10. According to the embodiment shown in FIG. 2, secondary Joule-Thomson heat exchanger 200c is located within housing 3, includes a chamber 21 defined by the inner walls of passageway 20, and preferably includes an orifice 18 located preferably at the lower end of spiral tube 14a. The optional spiral construction of spiral tube 14*a* is designed and constructed as heat-exchanging configuration 40*a*, facilitating the exchange of heat between spiral tube 14*a* and second passageway 16, and as heat-exchanging configuration 40*b* facilitating the exchange of heat between spiral tube 14*a* and passageway 20.

When a high-pressure cooling gas such as argon passes through orifice 18 it expands and is thereby cooled. The expanded gas may liquefy so as to form a cryogenic pool within chamber 21. The cooled expanded gas, and a cryogenic pool of liquefied gas which may form, effectively cool passageway 20, thereby precooling the gas flowing within spiral tube 14*a*. When a high-pressure heating gas such as helium expands through orifice 18 it heats chamber 21 and passageway 20, thereby effectively preheating the gas flowing within spiral tube 14*a*.

Thus, gas flowing through spiral tube 14*a* is effectively pre-cooled or pre-heated by exchanging heat with third passageway 20. Furthermore, the gas flowing through spiral tube 14*a* and strait tube 14*b* exchanges heat with second passageway 16 which contains cooled (or heated) gas coming from operating head 4.

A cryosurgery device according to the present invention enables to effectively and quickly produce the desired freezing effect and to quickly inverse from cooling to heating so as to prevent sticking of the operating head to the tissue.

A cryosurgery device according to the present invention also enables to induce fast cyclical temperature changes in a deployed cryoprobe, such that a temperature of the probe alternates rapidly between a temperature of approximately 0° C. and a temperature below −40° C. This cryosurgical technique has been found useful in a variety of cryosurgical situations.

According to another embodiment (not shown), first passageway 10 may include a plurality of orifices located along spiral tube 14*a* and strait tube 14*b*. Further, a device according to the present invention may include a plurality of Joule-Thomson heat exchangers for cooling or heating selected portions of the device, wherein each Joule-Thomson heat exchanger includes a plurality of orifices.

The heating mechanisms heretofore described, and the cooling mechanism heretofore described, may be separate mechanisms both contained within cryoprobe 104, yet in a preferred embodiment these mechanisms are a combined heating/cooling mechanism. First passageway 10 is designed and constructed so as to be coupleable to a first gas source, supplying a high-pressure cooling gas, and also to be coupleable to a second gas source supplying high-pressure heating gas. Thus coolable cryoprobe 104 may also be heatable.

Cryoprobe 104 preferably further comprises control elements for regulating the flow of gas from the first gas source and the second gas source. In a preferred embodiment, cryoprobe 104 includes a thermal sensor 30, such as, for example, a thermocouple, for monitoring the temperature within chamber 7 of operating head 4 at the distal portion of cryoprobe 104. An additional thermal sensor 32 may also be used to monitor temperature within chamber 21, or alternatively be placed at some other convenient position within cryoprobe 104 for monitoring local temperature conditions there.

Figure 3:
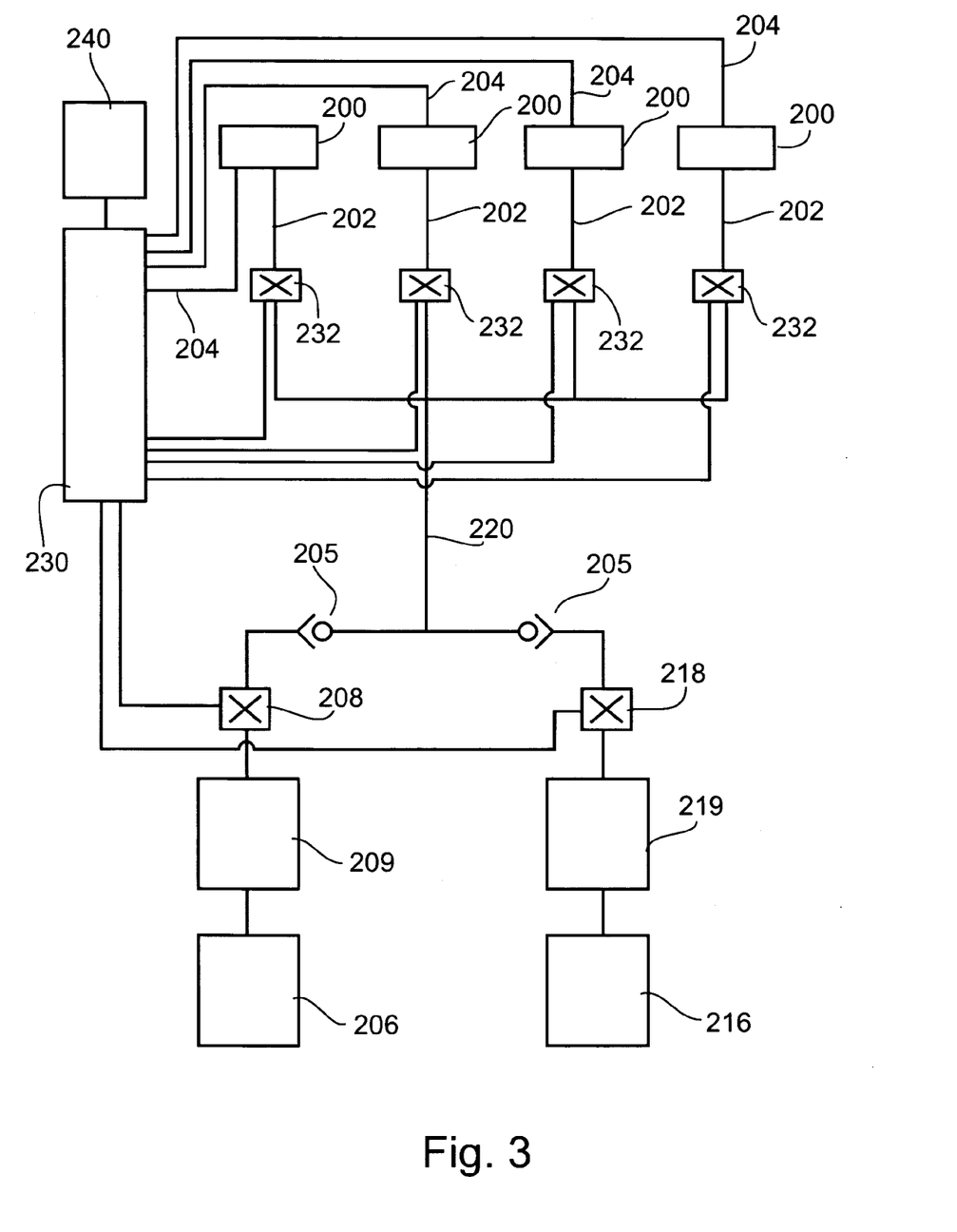
FIG. 3 is a schematic depiction showing mechanisms for control of delivery of high-pressure gases to a plurality of Joule-Thomson heat exchangers, according to the present invention.

FIG. 3 is a schematic drawing showing mechanisms for control of delivery of high-pressure gases to the plurality of Joule-Thomson heat exchangers 200 of cryoprobes 104 and/or introducer 100 employed in context of the present invention. Thus, heat exchangers 200 of FIG. 3 schematically represent individual Joule-Thomson heat exchange mechanisms herein described, such as a Joule-Thomson heat exchanger 200*a* of introducer 100 shown in FIG. 1 and in FIG. 4, and Joule-Thomson heat exchangers 200*b* and 200*c* of individual cryoprobes 104 shown in FIG. 2.

Each Joule-Thomson heat exchanger 200 is coupled to a passageway 202 for supplying high-pressure gas thereto. A passageway 202, for example, would be coupled to each gas input passageway 10 of individual cryoprobes 104, as shown in FIG. 2. A passageway 202 would similarly be coupled to the gas input passageway 310 of heat exchanger 200*a*, shown in detail in FIG. 4.

Figure 4:
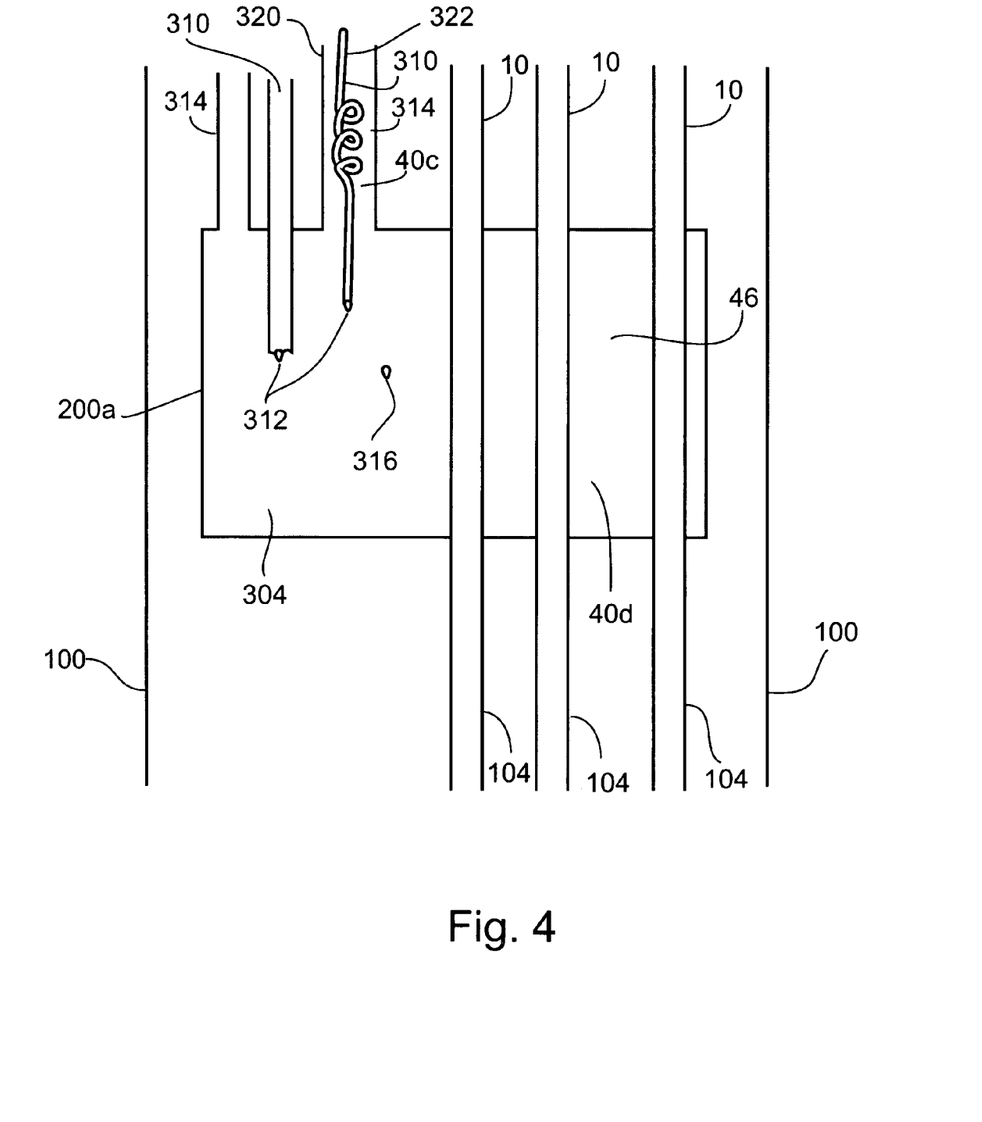
FIG. 4 is a detail view of a part of an introducer for introducing a plurality of cryoprobes into a body for effecting cryoablation, showing a Joule-Thomson heat exchanger within the introducer, according to the present invention.

Each heat exchanger 200 also optionally includes a thermal sensor which monitors temperatures therewithin or in its vicinity. Each such thermal sensor connects to an electrical feedback connection 204 which thereby receives information about the temperatures within heat exchangers 200. Electrical feedback connections 204 may be direct electrical connections, or other connections capable of transmitting data, such as infra-red connections. Thus, feedback connections 204 electrically connect with thermal sensors 30 and 32 of individual cryoprobes 104 as shown in FIG. 2, and with thermal sensor 316 of introducer 100 as shown in FIG. 4.

In FIG. 3, high-pressure heating gas source 206 supplies gas through control valve 208 and through a one-way valve 205 to common gas feed line s 220. Optional compressor 209 may be used to compress gases from source 206 to pressures higher than that supplied by source 206. Similarly, high-pressure cooling gas source 216 supplies gas through control valve 218 and one-way valve 205 to common gas feed line 220. Optional compressor 219 may be used to compress gas from source 216 to pressures higher than that supplied by source 216.

Optional control unit 230 is for controlling valves 208 and 218, thereby controlling a flow of gas from the gas sources into common gas feed line 220. Control unit 230 is also for controlling individual valves 232, thereby regulating the flow of gas into each Joule-Thomson heat exchanger 200.

Control unit 230 receives control instructions from a control input unit 240, which may include an operator's interface and optional computational and memory systems for supplying pre-programmed instructions. Control input unit 240 may connect directly to control unit 230, or control input unit 240 may be more or less remote from control unit 230 and communicate with control unit 230 using remote communication, such as radio or infra-red communication, or some other form of data communication. Control unit 230 may further communicate with, and receive control instructions from, a plurality of control input units 240.

Control unit 230 also receives feedback information from feedback connections 204 reporting temperatures within heat exchangers 200 (e.g., from thermal sensors 30, 32 and 316) or from other parts of the apparatus. Control unit 230, under instructions from control input unit 240 relating to the desired temperatures, opens and closes valves 208, 218, and 232 to control the flow of heating and cooling gasses to heat exchangers 200.

Joule-Thomson heat exchangers 200 heat and cool individual cryoprobes 104. Optionally, Joule-Thomson heat exchanger 200*a* of introducer 100 further preheats heating gasses and precools cooling gasses as they pass through Joule-Thomson heat exchanger 200*a* of introducer 100 on their way towards the Joule-Thomson heat exchangers 200*b* and 200*c* of individual to cryoprobes 104.

Optional Joule-Thomson heat exchanger 200*a*, which appears in a simplified form in FIG. 1, is presented in additional detail in FIG. 4, according to a preferred embodiment of the present invention.

FIG. 4 shows a portion of an introducer 100. Passageways 10, which serve for passing gas from high-pressure gas sources outside introducer 100 to cryoprobes 104, are situated near or within a chamber 304 within hollow 102 of introducer 100. Gas input passageway 310 provides high-pressure cooling or heating gasses which pass from passageway 310 through Joule-Thomson orifice 312, and expand into chamber 304. Cooling gasses passing from passageway 310 through Joule-Thomson orifice 312 expand and are thereby cooled and may liquefy. Cooling gasses cooled by expansion, and a cryogenic pool of liquefied gasses which may form, cool chamber 304. Heating gasses, which have an inversion temperature lower than the temperature obtained by liquefaction of the cooling gasses, pass from passageway 310 through Joule-Thomson orifice 312 and heat chamber 304. The gasses are subsequently exhausted to the atmosphere through passageway 314. Optional thermal sensor 316, which may be a thermocouple, monitors temperatures in chamber 304 and connects to electrical feedback connection 204 shown in FIG. 3.

In a preferred embodiment, heat exchanger 200a includes a heat-exchanging configuration 40c for facilitating exchange of heat between incoming gasses entering heat exchanger 200a through passageway 310 and exhaust gasses being exhausted to the atmosphere through passageway 314 after passing through Joule-Thomson orifice 312. In this embodiment passageway 310 for incoming gasses and passageway 314 for exhaust gasses are constructed of heat conducting material, such as a metal, and are constructed contiguous to each other, or wrapped one around the other. In an alternative construction of heat-exchanging configuration 40c, passageway 314 is implemented as a porous matrix 320 through which expanded gasses are exhausted to atmosphere. In this construction, passageway 310 is implemented as conduit 322 for incoming gasses formed within porous matrix 320. Conduit 322 may be formed as a straight conduit tunneling through porous matrix 320, or it may be formed as a spiral conduit integrated with porous matrix 320.

Heating gasses being exhausted through passage 314 after having passed through Joule-Thomson orifice 312 are hotter than incoming heating gasses entering through passageway 310. Consequently, exchange of heat between passageway 310 and passageway 314 has the effect of preheating incoming heating gasses, thereby enhancing efficiency of the apparatus.

Similarly, cooling gasses being exhausted through passage 314 after having passed through Joule-Thomson orifice 312 are colder than incoming cooling gasses entering through passageway 310. Consequently, exchange of heat between passageway 310 and passageway 314 has the effect of pre-cooling incoming cooling gasses, thereby enhancing efficiency of the apparatus.

Passageways 10 are preferably made of a thermally conducting material, such as a metal. Consequently, heating or cooling chamber 304 pre-heats or pre-cools the gasses passing through passageways 10 towards cryoprobes 104. Thus, the arrangement here described constitutes a heat-exchanging configuration 40d, for facilitating exchange of heat between heating and cooling chamber 304 and gas passing through passageways 10. In an alternate construction, heat-exchange configuration 40d is formed by implementing a portion of passageways 10 as either straight or spiral conduits tunneling through a porous matrix 46 occupying a portion of chamber 304. In yet another alternative arrangement, cryoprobes 104 themselves pass through chamber 304, resulting a similar pre-heating or pre-cooling effect. Chamber 304 may also be designed and constructed such that heating and cooling of chamber 304 has the effect of heating and cooling all or most of hollow 102 of introducer 100, and, as a result, all or most of the contents thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cryosurgery apparatus comprising:
   (a) an introducer for insertion into body tissues to an intended site of cryoblation, the introducer comprising
      (i) a hollow, wherein said hollow is partitioned into a plurality of longitudinal compartments; and
      (ii) a Joule-Thomson heat exchanger for heating or cooling at least a portion of said hollow; and
   (b) a plurality of cryoprobes, each cryoprobe positioned in a respective one of the plurality of longitudinal compartments, each of the cryoprobes for effecting cryoablation of body tissues.

2. The cryosurgery apparatus of claim 1, wherein the plurality of cryoprobes inserted in the plurality of longitudinal compartments are operable to deploy from a distal portion of the introducer at a plurality of angles with respect to a longitudinal axis of the introducer.

3. The cryosurgery apparatus of claim 2 wherein, the plurality of angles differ one from another with respect to direction.

4. The cryosurgery apparatus of claim 2, wherein the plurality of angles are predetermined.

5. The cryosurgery apparatus of claim 1, wherein the plurality of cryoprobes are operable to advance, during a deployment from a distal portion of the introducer, in a plurality of different directions.

6. The cryosurgery apparatus of claim 5, wherein the plurality of cryoprobes are designed and constructed to be deployed laterally away from the distal portion to form a predetermined arrangement of deployed cryoprobes.

7. The cryosurgery apparatus of claim 1, wherein the introducer further comprises a distal portion through which the plurality of longitudinal compartments extend.

8. The cryosurgery apparatus of claim 1, wherein the introducer has a distal end formed with a plurality of openings for a deployment therethrough of the plurality of cryoprobes.

9. The cryosurgery apparatus of claim 8, wherein each of the plurality of cryoprobes is retractable and advanceable in and out of a respective one of the plurality of openings.

10. The cryosurgery apparatus of claim 9, further comprising an advancing and retracting member operably coupled to at least one cryoprobe of the plurality of cryoprobes.

11. The cryosurgery apparatus of claim 10, wherein the advancing and retracting member is operably coupled to a plurality of cryoprobes of the plurality of cryoprobes.

12. The cryosurgery apparatus of claim 1, wherein the introducer has a sharp distal portion for penetrating body tissues upon insertion of the introducer.

13. The cryosurgery apparatus of claim 1, wherein each of the plurality of longitudinal compartments has a distal opening through which the cryoprobe contained therein may be deployed into body tissue when a distal end of the introducer is inserted into body tissues.

14. The cryosurgery apparatus of claim 1, wherein the introducer includes thermal insulation to insulate the hollow from body tissues when the introducer is inserted into body tissues.

15. The cryosurgery apparatus of claim 1, wherein the Joule-Thomson heat exchanger is configured for heating or cooling the plurality of cryoprobes positioned within the plurality of longitudinal compartments of said hollow.

* * * * *